(12) United States Patent
Grundfest et al.

(10) Patent No.: US 10,041,883 B2
(45) Date of Patent: Aug. 7, 2018

(54) SYSTEM AND METHOD FOR TIME-RESOLVED FLUORESCENCE IMAGING AND PULSE SHAPING

(71) Applicant: THE REGENTS OF THE UNIVERSITY OF CALIFORNIA, Oakland, CA (US)

(72) Inventors: Warren S. Grundfest, Los Angeles, CA (US); Oscar M. Stafsudd, Los Angeles, CA (US); Pei-Chi Jiang, Los Angeles, CA (US); Asael Papour, Los Angeles, CA (US); Zachary Deis Taylor, Poway, CA (US); Maie St. John, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 646 days.

(21) Appl. No.: 14/472,735

(22) Filed: Aug. 29, 2014

(65) Prior Publication Data
US 2015/0053871 A1 Feb. 26, 2015

Related U.S. Application Data

(63) Continuation of application No. PCT/US2013/028758, filed on Mar. 1, 2013.
(Continued)

(51) Int. Cl.
*G01J 1/58* (2006.01)
*G01N 21/64* (2006.01)
*G02B 21/16* (2006.01)

(52) U.S. Cl.
CPC ..... *G01N 21/6408* (2013.01); *G01N 21/6428* (2013.01); *G01N 21/6447* (2013.01);
(Continued)

(58) Field of Classification Search
CPC ....... G01N 21/6408; G01N 2021/6413; G01N 21/6486; G01N 2021/641
See application file for complete search history.

(56) References Cited

U.S. PATENT DOCUMENTS

| | | |
|---|---|---|
| 4,785,495 A | 11/1988 | Dellis |
| 6,272,376 B1 | 8/2001 | Marcu et al. |

(Continued)

FOREIGN PATENT DOCUMENTS

| | | |
|---|---|---|
| EP | 0 263 037 A2 | 4/1988 |
| EP | 1686685 A2 | 8/2006 |

(Continued)

OTHER PUBLICATIONS

Gramatikov, "Modern technologies for retinal scanning and imaging: an introduction for the biomedical engineer," Biomedical Engineering OnLine 2014, vol. 13, pp. 52.
(Continued)

*Primary Examiner* — Kenneth J Malkowski
(74) *Attorney, Agent, or Firm* — O'Banion & Ritchey LLP; John P. O'Banion

(57) ABSTRACT

A time-resolved fluorescence imaging (TRFI) system that images a target medium without lifetime fitting. Instead of extracting the lifetime precisely, the system images the fluorophore distribution to allow for a simple and accurate method to obtain the fluorescence image without lifetime-extraction for time-resolved fluorescence imaging. An illumination source circuit for TRFI is also disclosed that shapes the excitation pulse. In one embodiment, the illumination source comprises an LED and stub line configured for generating a linear decay profile.

12 Claims, 10 Drawing Sheets

Related U.S. Application Data

(60) Provisional application No. 61/605,844, filed on Mar. 2, 2012.

(52) U.S. Cl.
CPC ..... *G01N 21/6458* (2013.01); *G01N 21/6486* (2013.01); *G02B 21/16* (2013.01); *G01N 2021/6413* (2013.01); *G01N 2021/6441* (2013.01); *G01N 2201/062* (2013.01); *G01N 2201/0621* (2013.01)

(56) References Cited

U.S. PATENT DOCUMENTS

| 7,648,239 | B2 | 1/2010 | Spaide | |
|---|---|---|---|---|
| 7,890,157 | B2 | 2/2011 | Jo et al. | |
| 2001/0011930 | A1* | 8/2001 | Kintis | H03K 5/12 333/20 |
| 2006/0158277 | A1* | 7/2006 | Mrozek | H03B 25/00 333/20 |
| 2012/0101371 | A1 | 4/2012 | Verdooner | |
| 2012/0276578 | A1 | 11/2012 | Stringari et al. | |

FOREIGN PATENT DOCUMENTS

| EP | 2365338 A1 | 9/2011 |
|---|---|---|
| EP | 2414818 A1 | 2/2012 |
| WO | 2006-127967 A1 | 11/2006 |
| WO | 2011/135049 A1 | 11/2011 |
| WO | 2013 131062 A1 | 9/2013 |

OTHER PUBLICATIONS

Provoost, Jan "Bringing hyperspectral imaging to point-of-care medical applications" Medical Design, Sep. 4, 2012, pp. 1-5.
Wikipedia, "Fluorescence-lifetime imaging microscopy" retrieved on Jan. 31, 2015, http://en.wikipedia.org/wiki/Fluorescence-lifetime_imaging_microscopy.
Dehoog and Schwiegerling "Fundus camera systems: a comparative analysis" Appl Opt. Jan. 10, 2009; 48 (2): 221-228.
Aetna, "Clinical Policy Bulletin: Optic Nerve and Retinal Imaging Methods" 2001-2015, retrieved from: http://www.aetna.com/cpb/medical/data/300_399/0344.html, pp. 1-20.
Saine and Tyler "Fundus Photography Overview" Excerpted from: Ophthalmic Photography: Retinal Photography, Angiography, and Electronic Imaging, 2nd Edition, Boston: Butterworth-Heinemann, 2001. p. 424.
Sherman et al., "Abstract—Normalized fluorescence lifetime imaging for tumor identification and margin delineation," Proc. SPIE 8572, Advanced Biomedical and Clinical Diagnostic Systems XI, 85721H (Mar. 22, 2013).
Korean Intellectual Property Office, International Search Report and Written Opinion dated Jun. 21, 2013 for corresponding international patent application No. PCT/US2013/028758 (pp. 1-9) and PCT Claims (pp. 10-18).
Suhling et al., "Time-resolved fluorescence microscopy," Photochemical & photobiological sciences, vol. 4, No. 1, pp. 13-22, Nov. 11, 2004.
Periasamy et al., "Time-resolved fluorescence lifetime imaging microscopy using a picoseconds pulsed tunable dye laser system," Review of Scientific Instruments, vol. 67, No. 10, pp. 3722-3731, Jun. 24, 1996.
Pfeifer, et al., "Improved Routine Bio-Medical and Bio-Analytical Online Fluorescence Measurements Using Fluorescence Lifetime Resolution," Journal of Fluorescence, vol. 15, No. 3, May 2005.
McGinty, et al., "Wide-field fluorescence lifetime imaging of cancer," Biomedical Optics Express, vol. 1, No. 2, pp. 627, Sep. 2010.
Australian Government IP Australia, "Patent Examination Report No. 1", related Australian Patent Appln. No. 2013225655, dated Jan. 13, 2016, pp. 1-3, with claims examined, pp. 4-12.
European Patent Office (EPO), "Supplementary Partial European Search Report", related EPO Patent Appln. No. EP 13 75 5562, dated Sep. 14, 2015, pp. 1-4, with claims searched, pp. 5-9.
European Patent Office (EPO), "Supplementary European Search Report", related EPO Patent Appln. No. EP 13 75 5562, dated Dec. 18, 2015, pp. 1-17, with claims searched, pp. 18-22.
Dowling, K. et al., "Wholefield fluorescence lifetime imaging with picosecond resolution for biomedicine", Technical Digest, Summaries of Papers Presented at the Conference on Lasers and Electro-Optics, Conference Edition, 1998 Technical Digest Series, vol. 6 (IEEE Cat. No. 98CH36178), May 3, 1998 (May 3, 1998), XP055212722, DOI: 10.11009/CLEO.1998.676205, ISBN: 978-1-55-752339-6, p. 308 (1 page).
Kennedy, Gordon et al., "Fluorescence lifetime imaging using light emitting diodes", Journal of Physics D: Applied Physics, Institute of Physics Publishing Ltd., GB, vol. 41, No. 9, May 7, 2008 (May 7, 2008), p. 94012 (6 pages), XP020133627, ISSN: 0022-3727.
Kennedy, Gordon et al., "Fluorescence lifetime imaging using light-emitting diodes", Proceedings of SPIE, vol. 6443, Feb. 8, 2007 (Feb. 8, 2007), pp. 644315-644315-4 (4 pages), XP055221016, ISSN: 0277-786X, DOI: 10.1117/12.701088.
Jiang, Pei-Chi et al., "Quasi-real-time fluorescence imaging with lifetime dependent contrast", Journal of Biomedical Optics, vol. 16, No. 8, Aug. 2011 (Aug. 2011), p. 086001-1 (10 pages), XP055234355.
Japanese Patent Office (JPO), Notification of Reason(s) for Refusal dated Dec. 20, 2016, related Japanese Patent Application No. JP 2014-560114, pp. 1-2, with English-language translation, pp. 3-4, and with claims examined, pp. 5-8.
Japanese Patent Office (JPO), Notification of Reasons for Refusal dated Dec. 12, 2017, related Japanese patent application No. 2014-560114, pp. 1-3, English-language translation, pp. 4-6, with claims examined, p. 7-12.
European Patent Office (EPO), Communication pursuant to Article 94(3) EPC dated Nov. 11, 2017, related European application No. 13 755 562.9, pp. 1-7, with claims examined, pp. 8-11.
Papour, Asael, "Analysis and Optimization of a Lifetime Fluorescence System to Detect Structural Protein Signatures in Varying Host Mediums for Rapid Biomedical Imaging", University of California, Los Angeles, thesis submitted in partial satisfaction of the requirements for the degree Master of Science in Electrical Engineering, Dec. 3, 2012, 78 pages.

\* cited by examiner

SYSTEM AND METHOD FOR TIME-RESOLVED FLUORESCENCE IMAGING AND PULSE SHAPING

CROSS-REFERENCE TO RELATED APPLICATIONS

This application is a 35 U.S.C. § 111(a) continuation of PCT international application number PCT/US2013/028758 filed on Mar. 1, 2013, incorporated herein by reference in its entirety, which claims priority to, and the benefit of, U.S. provisional patent application Ser. No. 61/605,844 filed on Mar. 2, 2012, incorporated herein by reference in its entirety. Priority is claimed to each of the foregoing applications.

The above-referenced PCT international application was published as PCT International Publication No. WO 2013/131062 on Sep. 6, 2013, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to time-resolved fluorescence imaging, and more particularly to time-resolved fluorescence imaging without lifetime fitting.

2. Description of Related Art

To date, time-resolved fluorescence images are obtained by getting the lifetime pattern of the sample. Recent work in time-resolved fluorescence imaging (TRFI) has focused largely on efforts for developing mathematical algorithms to precisely extract the fluorescence lifetime from the fluorescence decay signals. After data of the fluorescence signal are acquired, the fluorescence data are analyzed and fluorescence lifetimes are estimated by fitting a decay model to the measured data. Time-resolved fluorescence data are usually complicated and are difficult to be graphically analyzed. Since the 1970s, researchers have proposed many methods and algorithms to analyze them. Today, nonlinear least squares (NLLS) is one of the most popular methods in fitting and analyzing biomedical data. Its concept is that a model starts with initial parameters and estimates the fluorescence lifetime by using iteration convolution to adjust the initial parameters and to find the best match between the measured data and the calculated data.

The time-resolved fluorescence signal of a fluorophore is usually a mono-exponential curve. However, since there is usually more than one kind of fluorophores in the specimen, the intensity decay curve is usually a combination of several exponential decay curves, which can be shown in Eq. 1:

$$I = \sum_n a_n \cdot e^{\frac{-t}{\tau_n}} \qquad \text{Eq. 1}$$

where a is the amplitude and $\tau$ is the decay constant, or fluorescence lifetime.

Lifetime extraction of this multi-exponential curve is complicated and time-consuming. To make it more complicated, lifetime-extraction to obtain fluorescence images may not be reliable. Any fluorescence decay fitting and lifetime estimation methods have resolution limits. When two or more fluorescence lifetimes are closely spaced, NLLS becomes limited.

FIG. 1A and FIG. 1B show multi-exponential decay curves (in linear scale and logarithmic scale, respectively) composed of two fluorescence lifetimes (dashed and solid lines). The two lines almost perfectly overlap, although they are composed of two different sets of lifetimes. Thus, in order to accurately extract the lifetimes, complicated algorithms are developed, requiring long calculation times. The situation can be even worse when there is noise in the fluorescence signal (which is the general case), making lifetime-extraction more unreliable.

Accordingly, an object of the present invention is to overcome the restrictions of lifetime-extraction-based TRFI by obtaining time-resolved fluorescence images via low-computation calculations without lifetime calculation.

BRIEF SUMMARY OF THE INVENTION

An aspect of the present invention is a time-resolved fluorescence imaging (TRFI) system that does not need lifetime fitting. Instead of extracting the lifetime precisely, the main focus of the systems and methods of the present invention is to obtain the image of the fluorophore distribution to allow for a simple and accurate method to obtain the fluorescence image without lifetime-extraction for time-resolved fluorescence imaging.

Another aspect is an illumination source circuit for TRFI that shapes the excitation pulse. In one embodiment, the illumination source comprises an LED and stub line configured for generating a linear decay profile.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 13:
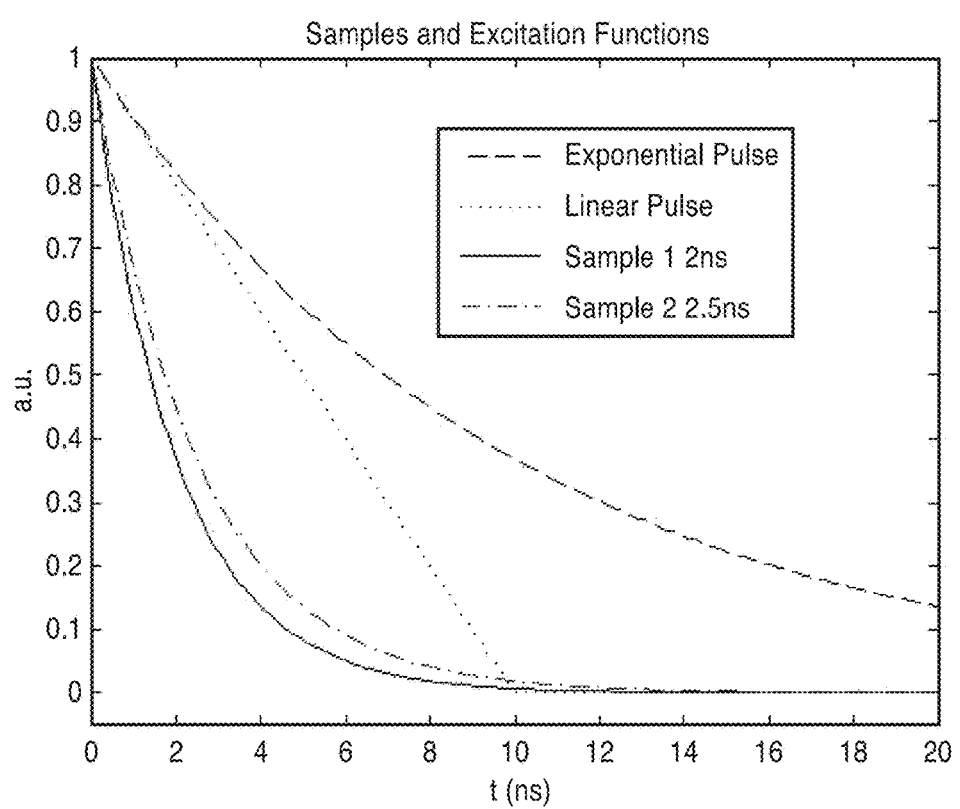

FIG. 13 is a plot showing an exponential pulse (10 ns decay coefficient) and a linear pulse (slope−10 ns), along with 2 samples having 2 ns and 2.5 ns exponential decay coefficient.

Figure 14:
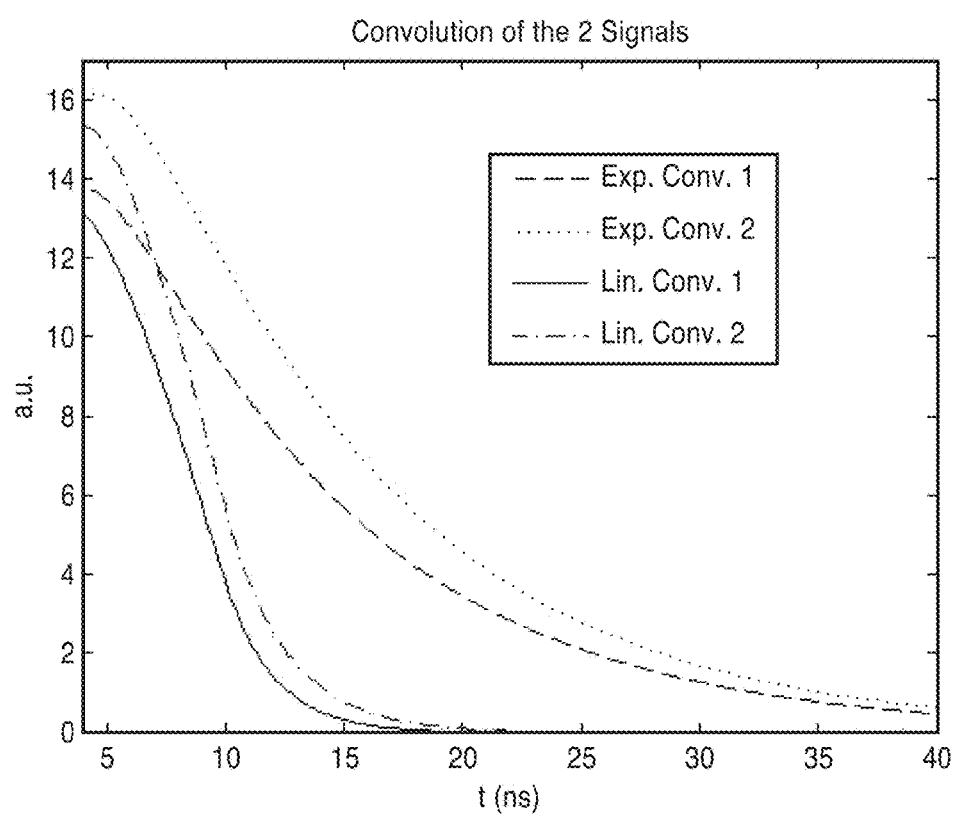

FIG. 14 shows a plot of the convolution product of each excitation pulse of two samples to simulate the actual measured signals of the FLIM system.

Figure 5:
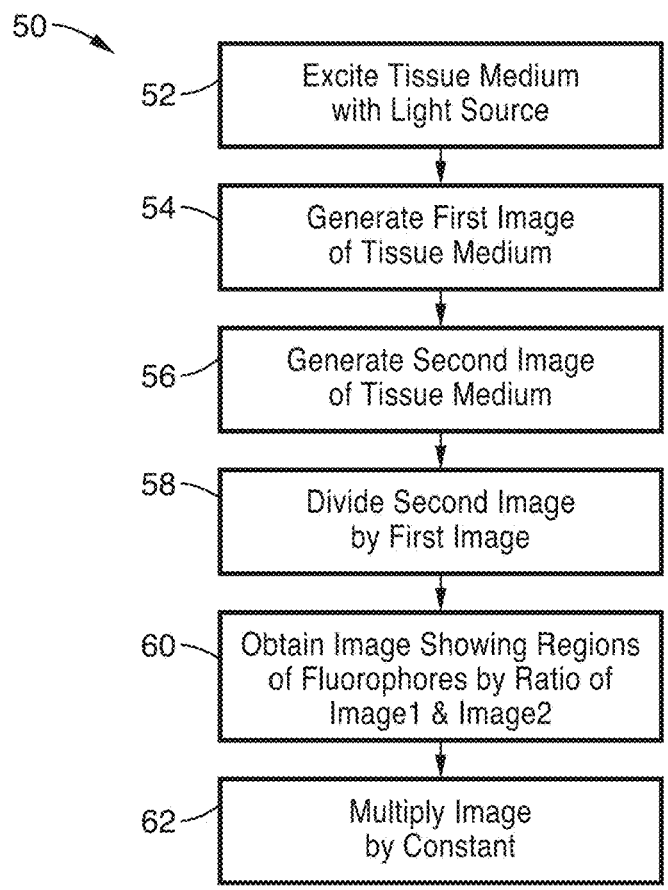
FIG. 5 is a flow diagram of a division-based method of the present invention for performing TRFI without lifetime fitting.
Figure 15:
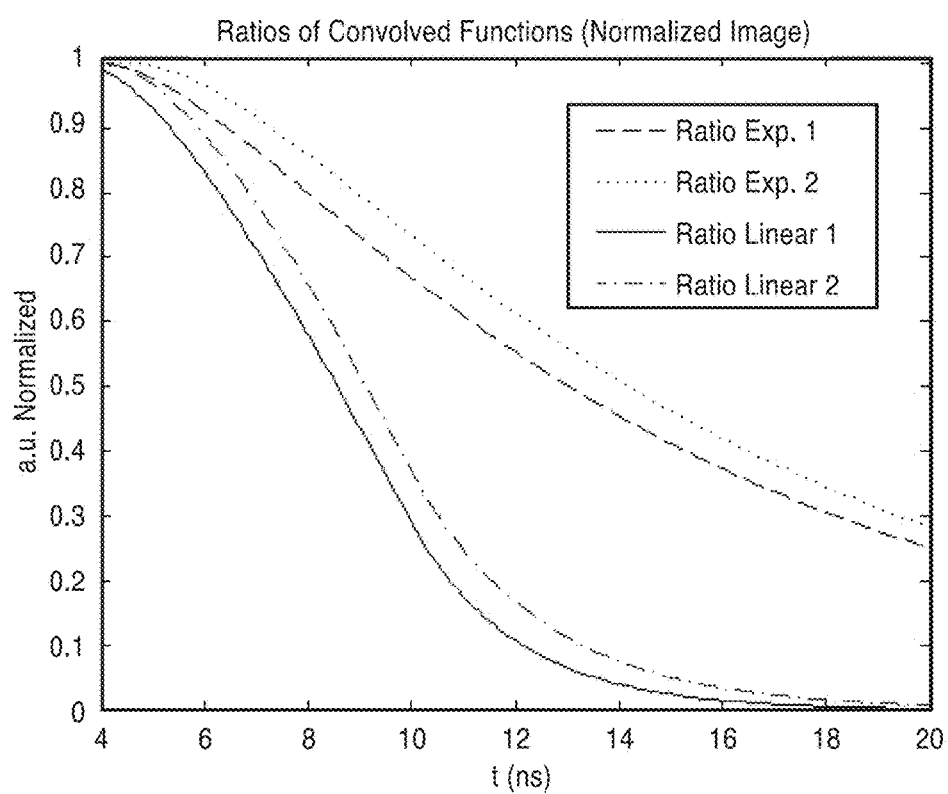

FIG. 15 shows a plot of two samples after normalization according to the method of FIG. 5 for excitation pulses having both linear and exponential decay.

Figure 1A:
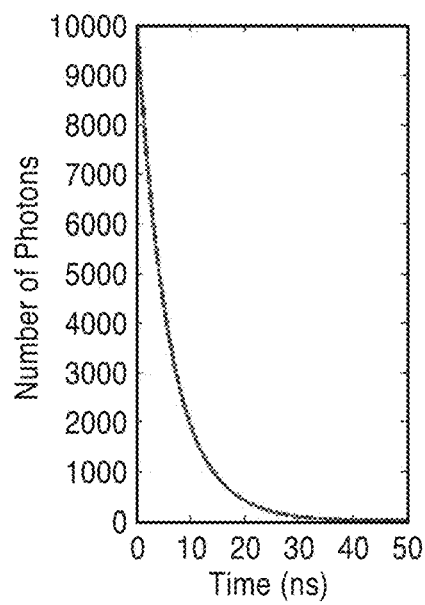
FIG. 1A and FIG. 1B show multi-exponential decay curves (in linear scale and logarithmic scale, respectively) composed of two fluorescence lifetimes.
Figure 1B:
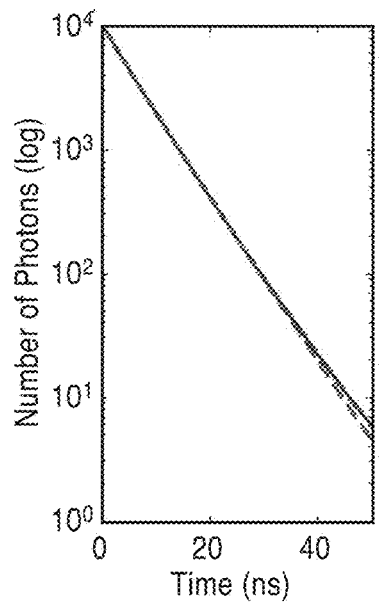
Figure 2:
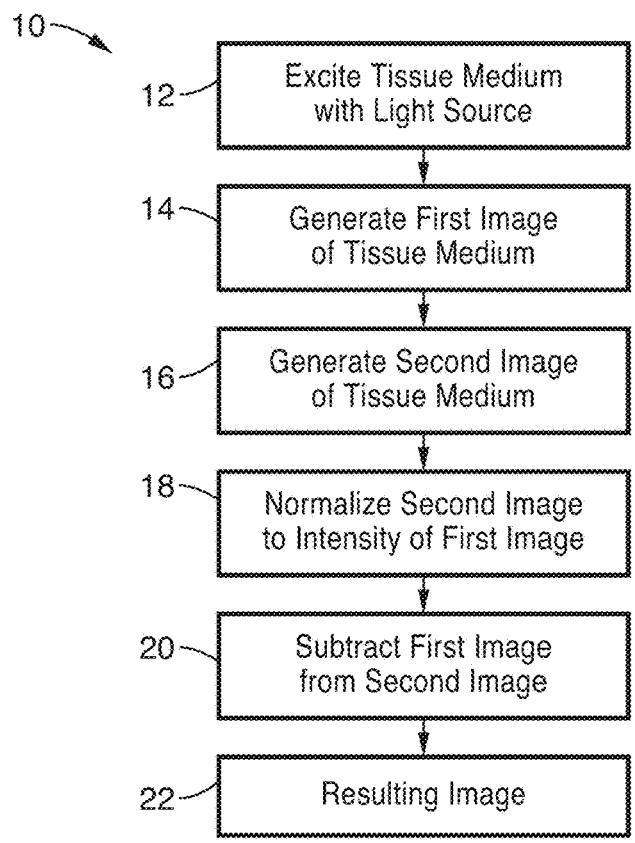
FIG. 2 is a schematic flow diagram of a subtraction-based method of the present invention for performing TRFI without lifetime fitting.
Figure 16:
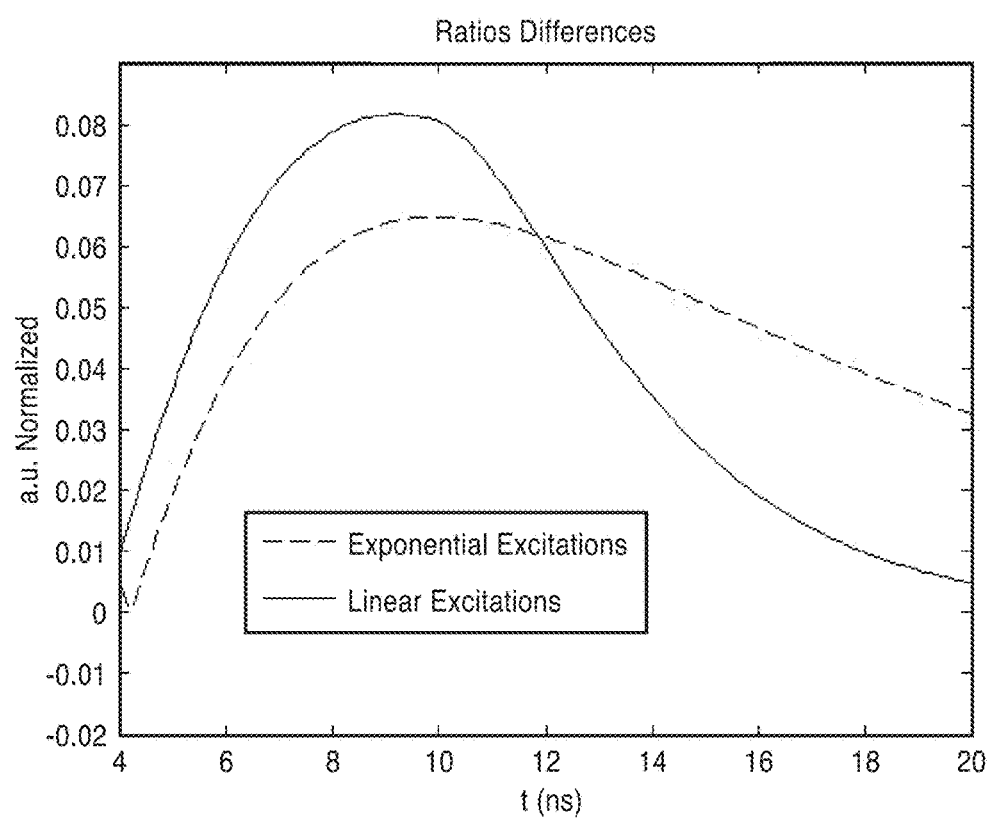

FIG. 16 shows a plot of subtraction of two signals from the same excitation source according to the method of FIG. 2 for excitation pulses having both linear and exponential decay.

DETAILED DESCRIPTION OF THE INVENTION

Figure 3:
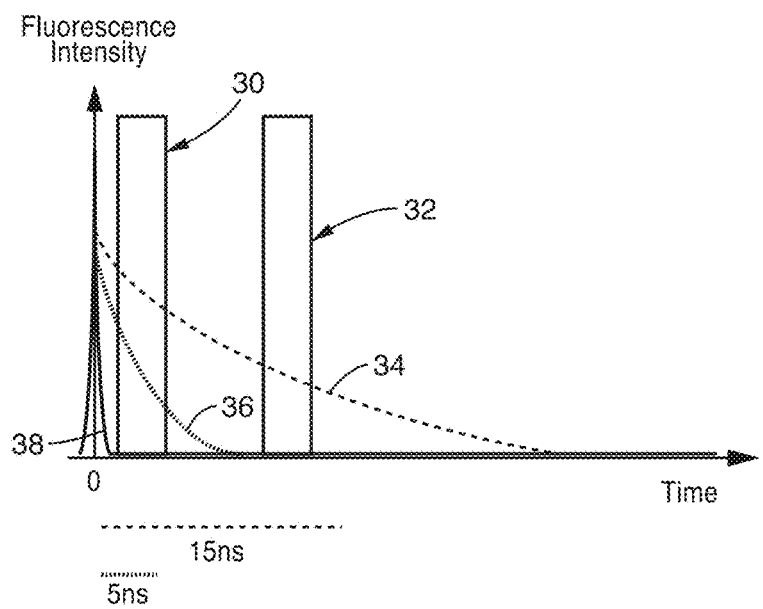
FIG. 3 is a schematic diagram of fluorescence signals with short and long lifetimes with respect to two images for use in the method of FIG. 2.
Figure 4:
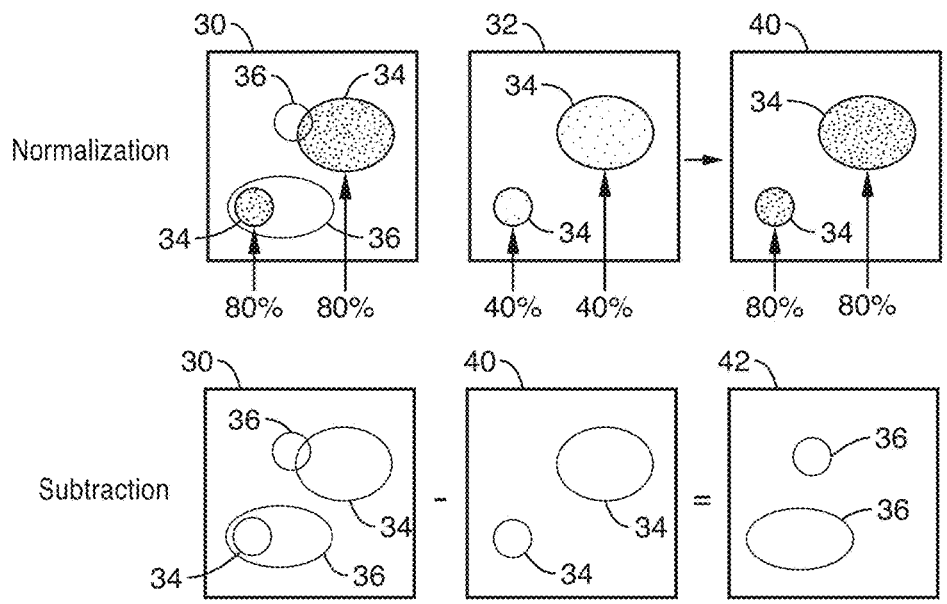
FIG. 4 is a schematic diagram of images obtained for use in the method of FIG. 2.
Figure 8:
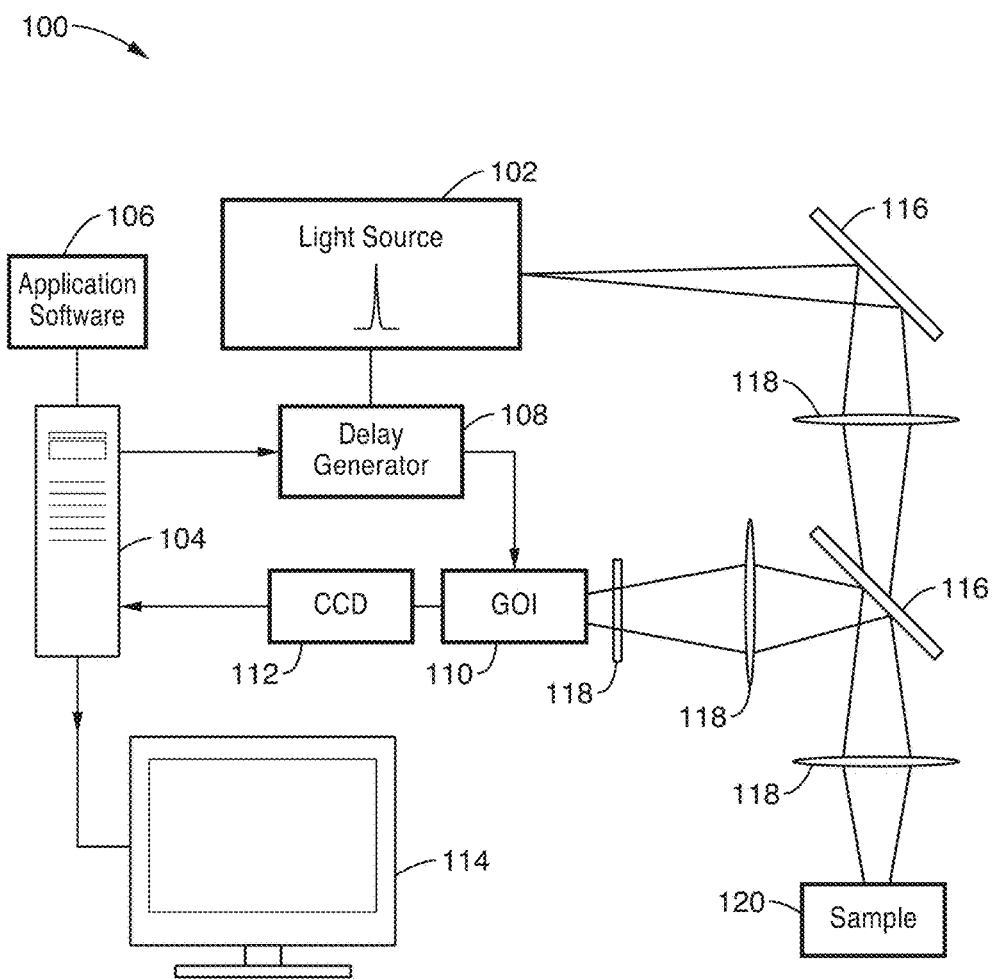
FIG. 8 shows an exemplary system for implementation of methods for TRFI without lifetime fitting in accordance with the present invention.

FIG. 2 through FIG. 4 illustrate a first method 10 of the present invention for performing TRFI without lifetime fitting. In the example shown in FIG. 2 through FIG. 4, we assume that there are two fluorophores in the specimen, one with longer fluorescence lifetime (shown via curve 34 in FIG. 3) and the other with a shorter one (shown via curve 36 in FIG. 3). Accordingly, the fluorescence intensity of the longer-lifetime fluorophore will decay slower. In method 10 of the present invention, two fluorescence images 30 and 32 are gated and sampled during the decay of the fluorescence signals after the specimen is excited by a light source at step 12. The curve for the excitation pulse 38 is shown in FIG. 8, and as will be described in further detail below, may be shaped to have a linear profile.

The first image 30 is recorded at step 14 when both the fluorescence signals 34 and 36 are still decaying. The second image 32 is recorded at step 16 while the shorter-lifetime fluorophore 36 stops fluorescing, thus only the image of the fluorophore with longer lifetime 34 is recorded (see FIG. 3).

In order to obtain the distribution of the shorter-lifetime fluorophore 36, the intensity of the second image 32 is first normalized to the intensity of the first image 30 at step 18 to generate a normalized image 40 of the fluorophore with longer lifetime 34. Next, at step 20, the first image 30 is then subtracted from the normalized second image 40. At step 22, the resulting image 42 contains only the distribution of the shorter-lifetime fluorophore 36, and the pattern of the longer-lifetime fluorophore 34 is gone. Thus, the method 10 of the present invention obtains individual information about the target medium via contrast in the medium constituents, rather than determining the decay lifetime of excited fluorophores.

Figure 6:
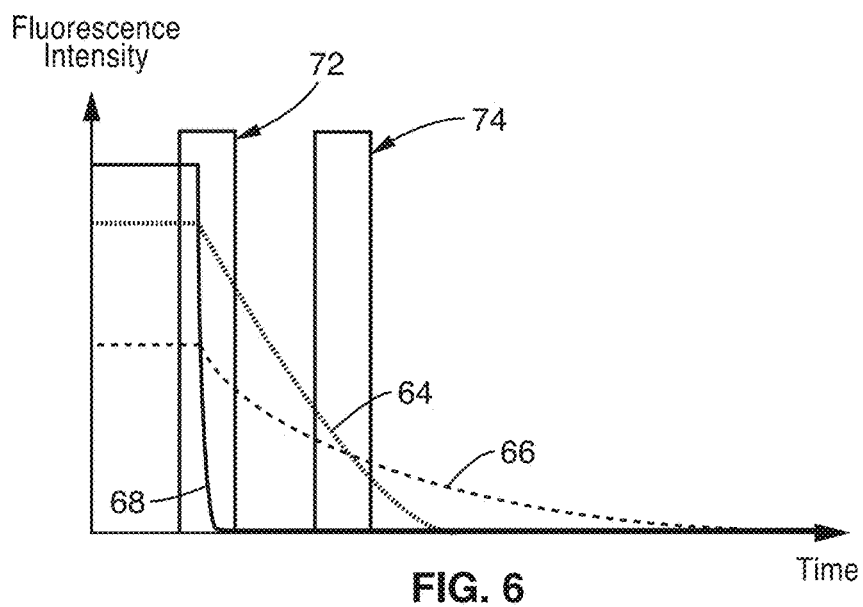
FIG. 6 is a schematic diagram of fluorescence signals with short and long lifetimes with respect to two images for use in the method of FIG. 5.
Figure 7:
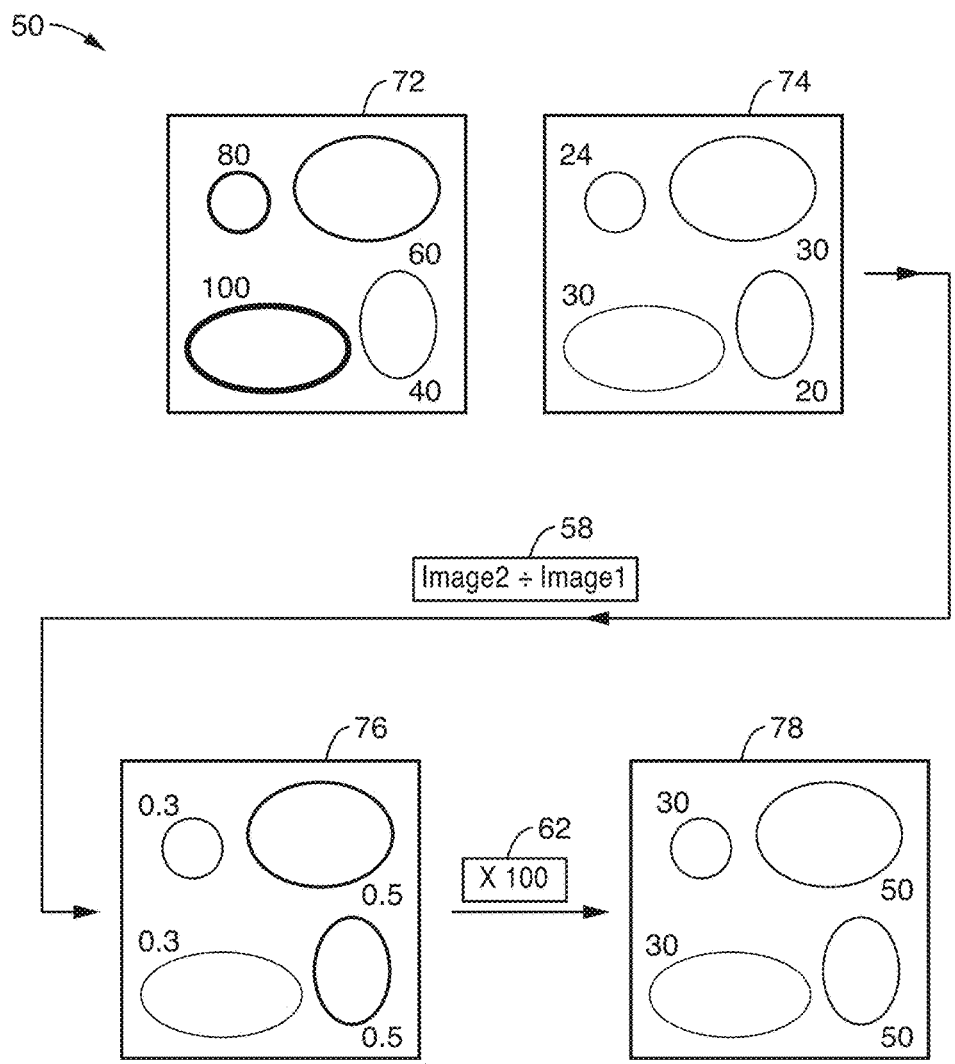
FIG. 7 is a schematic diagram of images obtained for use in the method of FIG. 5.

FIG. 5 through FIG. 7 show a second method 50 of the present invention for performing TRFI without lifetime fitting. In method 50, the decaying intensity is gated and sampled twice while both the fluorophores 64 and 66 are still fluorescing (see FIG. 6). Referring to FIG. 5 and FIG. 6, after the excitation pulse at step 52, two images are obtained. The first image 72 is obtained after pulse 68 at step 54, thus having a high fluorescence intensity. The second image 74 is then obtained at step 56 a set interval after the first image 72, and thus has a lower intensity than the first image 72.

At step 58, the second image 74 is divided by the first image 72, and a new image 76 is generated at step 60 showing the ratio of the two images. In the regions of the same kind of fluorophore, the ratio value will be the same, no matter what the initial intensity value is. At step 62, the differences are enhanced to generate image 78 by multiplying all pixels with a constant (e.g., 100× in FIG. 7) via the image processing software. The two regions at the left in image 72 represent the area of the shorter-lifetime fluorophore, while those at the right are the distribution of the longer-lifetime fluorophore. We can see that although all the circular regions have different intensities in image 72 and 74, they can be clearly classified after simple division and intensification.

The methods 10 and 50 shown in FIG. 2 through FIG. 7 are shown with respect to imaging two fluorophores. However, it is appreciated that the methods 10 and 50 may also be used for samples composed of more than two fluorophores by using multiple subtractions. For simplicity, the two-fluorophore sample is merely used as an example.

FIG. 8 shows an exemplary system 100 for implementation of TRFI methods 10, 50 without lifetime fitting in accordance with the present invention. System 100 comprises a light source 102 configured for generating an excitation pulse (e.g. pulse 38 in FIG. 3 and pulse 68 in FIG. 6) that is structured to generate a specific illumination profile to excite the fluorophores of the desired target medium (e.g. tissue). In a preferred embodiment, described in further detail below, the light source 102 comprises an LED. The light source 102 is coupled to a delay generator 108 and computer 104. Computer 104 is coupled to CCD array 112 for receiving signals from the excited medium or sample 120, and a processor configured to execute application software 106.

Application software 106 comprises algorithms/programming configured to shape the pulse from light source 102, as well as perform the operations of methods 10 and/or 50 for evaluating the images obtained from the excited medium to perform TRFI. The light source 102 generates excitation pulses into target sample 120 via a series of filters/lenses 118 and mirrors 116 (e.g. dichromatic mirror, etc.). The fluorescence signal from the excited sample 120 is detected from CCD array 112. In one embodiment, the fluorescence signal is gated, intensified, and recorded by an iCCD camera, which functions as a combination of a gated optical image intensifier 110 and a CCD camera 112. Data from the CCD is then transferred to the computer 104 for image processing and monitor 114 for display.

Figure 9A:
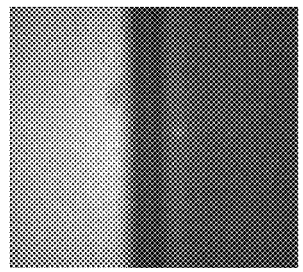
FIG. 9A through FIG. 9C show sampled and normalized images according to the method of FIG. 2.
Figure 9B:
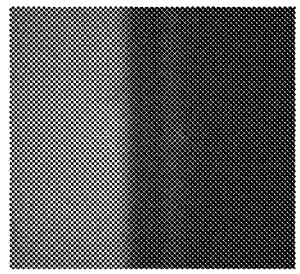
Figure 9C:
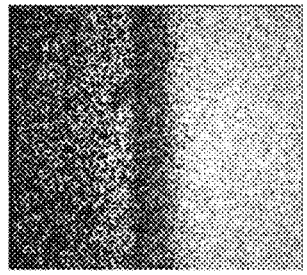

Referring now to FIG. 9A through FIG. 11C the methods 10, 50 of the present invention were tested using Fluorescein and Rhodamine-B as sample components of a target medium. The lifetime of Fluorescein is around 4.0 ns in the solvent of phosphate buffer pH 7.5, while the lifetime of Rhodamine-B is around 1.68 ns in water. The lifetime value, however, may change with various factors, such as solvent and concentration. The two materials were placed side by side and were first imaged using subtraction method 10 in accordance with the present invention. The data shows successful detection of one fluorophore from the other by normalizing and subtracting the two sampled images. FIG. 9A and FIG. 9B show two sampled images, with FIG. 9A being the image taken when both fluorophores were still fluorescing, and FIG. 9B being the image taken when Rhodamine-B decays to zero and only Fluorescein was still fluorescing. FIG. 9C is the image after normalization, subtraction and intensification of FIGS. 9A and 9B.

Figure 10A:
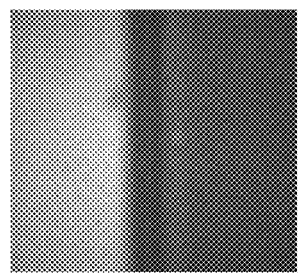
FIG. 10A through FIG. 10C show sampled and normalized images according to the method of FIG. 5.
Figure 10B:
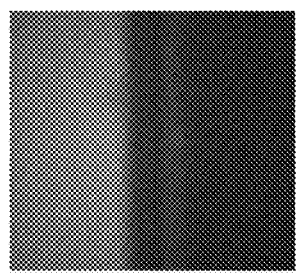
Figure 10C:
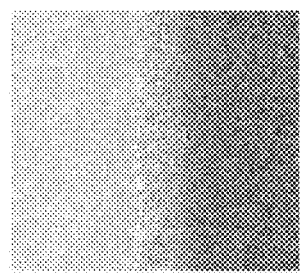
Figure 11A:
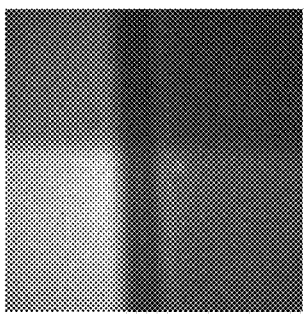
FIG. 11A through FIG. 11C show sampled and normalized images partially covered by an optical density according to the method of FIG. 5.
Figure 11B:
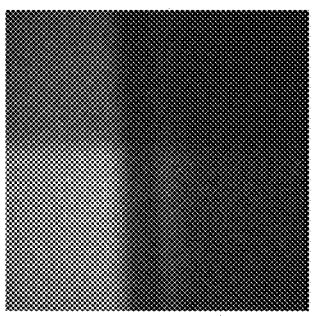
Figure 11C:
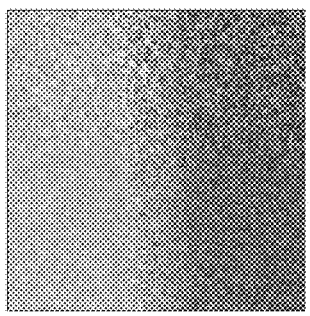

Method 50 was also tested with the same set of samples. Two fluorescence images were recorded while both fluorophores were still fluorescing. The images sampled at 26 ns and 40 ns after the excitation are shown in FIG. 10A and FIG. 10B, respectively. Dividing image of FIG. 10B by the image of FIG. 10A, and multiplying by a constant, we obtained the image of FIG. 10C. The data point of FIG. 10C represents the multiplication of the ratio of FIG. 10A and FIG. 10B.

Since the values of the ratios depend on the fluorescence lifetimes of the fluorophores, the different components are distinguishable, even though the intensity of the fluorescence signal is not uniformly distributed. The capability of method 50 is further shown FIG. 11A through 11C. An optical density was used to partially cover the sample. Therefore, the intensity of fluorescence signal will be non-uniform at each side on the sampled images, shown in FIG. 11A and FIG. 11B. However, by using method 50 of the present invention, we obtained an image in FIG. 11C that clearly distinguishes Fluorescein and Rhodamine-B, without the effect of the non-uniformity of the fluorescence intensity.

Figure 12:
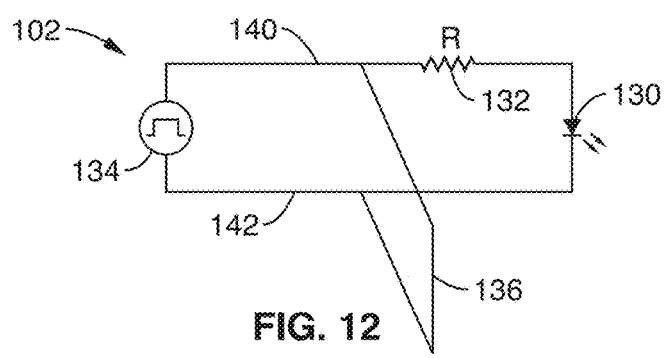
FIG. 12 illustrates a schematic view of a circuit diagram for an exemplary LED-based light source in accordance with the present invention.

FIG. 12 illustrates a circuit diagram of an exemplary pulse-shaping light source 102 in accordance with the present invention. The illumination source or circuit 102 comprises a light emitting element 130 that is coupled to a pulse generator 134 via transmission line 140, 142, and is configured to produce a specific illumination intensity profile (i.e. pulse shaping) that is optimal for the methods 10, 50 of the present invention, as well as existing TRFI systems. The circuit 102 optimally comprises a stub line 136, LED (light-emitting diode)-based light emitting element 130, and a resistive element 132.

The stub line 136 functions as a delay-line, negative loop-back and is connected to the terminals 140, 142 of the illumination circuit 102. The final optical impulse is formed by combining the pulse reflected from the short-circuited stub 136 and that transmitted across the junction between the short-circuited stub 136 and the transmission line 140,142.

A linearly decaying illumination profile of the illumination source, and in particular an illumination source 102 comprising an LED 130, can be achieved by using the above pulse-shaping configuration. A linear decay pulse is advantageous, since the pulse's decay slope is well defined and is finite. This makes de-convolving of optical pulses an easier task compared to non-linear decay profiles. In a preferred embodiment, pulses are structured with a cycle time longer than the pulse width.

It is appreciated that the circuit is optimally configured with a stub line 136 as shown in FIG. 12. However, it is appreciated that any element that is capable of shaping the pulse can be used using the following concept. The LED 130 illumination characteristic is governed by the recombination of electron hole pairs in the depletion region of the LED's p-n junction. With a given square pulse, the decay in intensity of the LED is described by the recombination time coefficient; an exponential decay function. A controlled linear illumination decay profile (or other shapes) can be achieved by the stub line 136, for example, acting as a passive delay line, depleting charge in the circuit and the p-n junction. Controlling the characteristics of the stub line 136 (e.g. shape, length, and material) and/or the pulse, a linear decay illumination profile can be achieved.

The desired reflection coefficient if the stub line may be modeled according to Eq. 2 as follows:

$$\Gamma = \Gamma_L e^{-2j\beta l} \qquad \text{Eq. 2}$$

where $\Gamma_L$ is the reflection coefficient at the load, l is the length of the line, and $\beta$ is the phase constant (which depends on the frequency). For distance calculations, a Smith chart can be used.

It is appreciated that while a linear decay profile is advantageous, the systems and methods of the present invention are not limited to a linear decay, as pulse splitting and various decay profiles can also be achieved.

Illumination circuit 102 may be used to drive LEDs as the light-emitting element 130, as well as other illuminating devices such as semiconductor lasers and other semiconductor light sources that exhibit a nonlinear luminosity decay profile. A finite optical pulse with a well-defined linearly decaying slope is difficult to achieve in such systems.

Since the operation of the LED 130 has intrinsic exponential decaying characteristics in the depletion region, even in a given square wave electronic signal input, an exponential decay of the illumination profile will be observed. Using a delay line loop to deplete the trailing edge charge in the circuit, e.g. via stub line 136, is an extremely efficient and easy way to deploy in discrete or modulated pulses illumination systems. The ability to adjust the stub line 136 length and resistance makes it ideal for controlling the shape of the decay profile, with the advantage of not paying penalty in pulse initial intensity, only in reducing the trailing edge intensity into a linear profile.

The auxiliary pulse generator 134 is capable of driving the illumination circuit 102 with adjustable pulse parameters, e.g. pulse length, amplitude and repetition rate are adjustable. For use in the methods 10 and 50 of the present invention for performing TRFI, the pulse widths generated from the circuit 102 are generally in the range of 0.5 nanoseconds (ns) or greater, and preferably in the range of 1 ns to 20 ns, and more preferably approximately 10 ns. This pulse width range is significantly longer than the typical laser-pulsed system for fluorescence lifetime measurements (which are generally in the picosecond range), and allows for much less expensive light sources such as LED's. It is appreciated that this range may vary according to the evaluated medium (e.g. tissue type, and other factors/parameters such as duty cycle, power, etc.). Generally, the shorter the pulse, the longer it takes to image. Accordingly, existing pulsed laser systems often take a minute or longer, while the methods 10, 50 of the present invention may contrast the medium in less than a second, even while using less "sophisticated" illumination sources such as LED's.

With respect to fluorescence lifetime imaging microscopy (FLIM), measurements of fluorescence lifetime using the pulsed LED circuit 102 of the present invention provide an economical alternative to existing pulsed-laser systems. Using the pulsed LED circuit 102 of the present invention in FLIM achieves superior analysis by simplifying the pulse analysis to give better measurements, and overcomes the deconvolution errors when fluorescent lifetimes are calculated. The linear luminosity decay profile generated from the pulsed LED circuit 102 of the present invention achieves better contrast in raw images, simplifies analysis, and reduces the computational power needed for image processing.

Referring now to FIG. 13 through FIG. 16, a series of experiments were conducted to illustrate the advantage of linear decay profile generated using the LED-pulsed circuit 102 over the typical exponential decay excitation pulse used in the art. The tests were conducted by simulating a measured pulse of two known samples.

FIG. 13 is a plot showing two excitation pulses: a first exponential pulse (10 ns decay coefficient), and a second linear pulse (slope–10 ns), along with 2 samples having a 2 ns and 2.5 ns exponential decay coefficient, respectively. All signals were normalized to eliminate amplitude variation and emphasize changes only due to lifetime's differences.

FIG. 14 shows the convolution product of each excitation pulse with the two samples, thus creating four decay curves, which simulates the actual measured signals of the FLIM system.

FIG. 15 shows a plot of two samples after normalization according to method 50 of the present invention for excitation pulses having both linear and exponential decay. FIG. 15 illustrates the result of dividing the points of the decay by the initial (highest) intensity, to get ratios of fluorescence for each point in time to the initial intensity. Four ratios are shown in the plot, wherein each point in the plot is a division product, with the highest intensity being 1, creating a normalized picture, due only to lifetime differences. This aids in eliminating differences in amplitude, and shows only the lifetime characteristics of each signal.

FIG. 16 shows a plot of subtraction of two signals from the same excitation source according to method 10 of the present invention for excitation pulses having both linear and exponential decay. FIG. 16 shows the ratios of the differences between each of the excitation sources, resulting in two graphs. Each graph is the result of subtraction of the two ratios with the same excitation function (e.g. linear vs. exponential). A larger discrepancy is preferred, since it will produce a sharper contrast image. As shown in FIG. 16, the differences of the linearly excited pulses (solid line) generated from the light source 102 are clearly larger than the exponentially excited pulses (dashed line) within the high signal-to-noise regime (4 ns-12 ns). In absolute numbers, the exponential decay pulse cannot overcome the linear decay pulse generated from the system of the present invention at any time. This shows the advantage in using linearly-modulated excitation pulse of the present invention over exponential pulse in the FLIM system.

As explained above, the methods of the present invention are capable of obtaining time-resolved fluorescence images without the need of extracting the fluorescence lifetime. No extra adjustment on the TRFI system 100 is required. However, the pulse-shaping light source of the present invention may be particularly beneficial in practicing the methods of the present invention. Comparing to the conventional TRFI, the systems and methods of the present invention are reliable, simple, straight-forward and time-saving.

In one aspect of the present invention, the systems and methods of the present invention are particularly adapted for imaging in biomedical applications. Such applications may include, but are not limited to: (1) cancer detection for a broad range of imaging procedures, both endoscopic and microscopic, (2) cosmetic application for determination of collagen and elastin ratio, and (3) identification of unknown substances in medical forensics.

However, it is appreciated that the systems and methods of the present invention may be used in any application where time-resolved fluorescence is contemplated, particularly in applications where obtaining contrast within the medium is an objective. Such uses may comprise non-biomedical applications, such as spectroscopy for combustion, vapors, etc. The CCD 112 may be coupled to a variety of objectives such as for a telescope, microscope, single lens reflex (SLR) camera, or the like for a number of difference applications.

The systems and methods of the present invention provide a faster, simpler, and more reliable way to obtain time-resolved fluorescence images. Fitting the decay curve to extract the fluorescence lifetime is difficult, time-consuming, and not reliable. The methods of the present invention provide rapid determination of the relative lifetime within an image, instead of extracting the value of the fluorescence lifetime. This is similar to X-ray imaging in which all points in the images are viewed relatively to their ability to absorb or transmit X-ray.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method for imaging a sample medium, the method comprising; exciting the sample medium with an excitation light pulse; generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore; generating a second image of the medium at a specified time subsequent to said first image, said second image comprising data relating to at least the first fluorophore; and generating a third image as a function of first image and the second image to identify a contrast between the first component and the second component within the medium.

2. A method as in any of the previous embodiments: wherein the second image is generated after decay of the second fluorophore such that data relating to the second fluorophore is absent from the second image; and wherein generating the third image comprises subtracting the first image from the second image such that data relating to the first fluorophore is absent from the second image.

3. A method as in any of the previous embodiments, wherein the second image is normalized to the intensity of the first image prior to subtracting the first image from the second image.

4. A method as in any of the previous embodiments: wherein the second image is generated while the first and second fluorophores are still decaying; wherein the second image further comprises data relating to the second fluorophore; and wherein generating the third image comprises dividing the second image by the first image.

5. A method as in any of the previous embodiments, further comprising: multiplying the third image by a constant.

6. A method as in any of the previous embodiments, wherein the sample medium comprises human tissue.

7. A system for imaging a sample medium, the system comprising: (a) a processor; and (b) programming executable on said processor and configured for: (i) exciting the sample medium with an excitation light pulse; (ii) generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore; (iii) generating a second image of the medium at a specified time subsequent to said first image, said second image comprising data relating to at least the first fluorophore; and (iv) generating a third image as a function of first image and the second image to identify a contrast between the first component and the second component within the medium.

8. A system as recited in claim 7: wherein the second image is generated after decay of the second fluorophore such that data relating to the second fluorophore is absent from the second image; and wherein generating the third image comprises subtracting the first image from the second image such that data relating to the first fluorophore is absent from the second image.

9. A system as in any of the previous embodiments, wherein the second image is normalized to an intensity of the first image prior to subtracting the first image from the second image.

10. A system as in any of the previous embodiments: wherein the second image is generated while the first and second fluorophores are still decaying; wherein the second image further comprises data relating to the second fluorophore; and wherein generating the third image comprises dividing the second image by the first image.

11. A system as in any of the previous embodiments, wherein the programming is further configured for: multiplying the third image by a constant.

12. A system as in any of the previous embodiments, wherein the sample medium comprises human tissue.

13. An apparatus for time-resolved fluorescence imaging of a sample medium, the apparatus comprising: a light-emitting element configured to generate an excitation pulse into the medium; a pulse generator coupled to the light-emitting element via a transmission line; and a delay line coupled to the transmission line; wherein the delay line is configured to generate a reflected pulse into the transmission line to shape a decay profile of the excitation pulse.

14. An apparatus as in any of the previous embodiments, wherein the delay line functions as a passive negative loop-back to deplete a trailing-edge charge within the light-emitting element.

15. An apparatus as in any of the previous embodiments, wherein the delay line comprises a stub line.

16. An apparatus as in any of the previous embodiments, wherein the reflected pulse from the delay line is configured to generate an excitation pulse with a controlled linear decay illumination profile.

17. An apparatus as in any of the previous embodiments, wherein the shape and size of the stub line are configured to control the shape of the decay illumination profile.

18. An apparatus as in any of the previous embodiments, wherein the light-emitting element comprises an LED.

19. An apparatus as in any of the previous embodiments: wherein the medium comprises human tissue; and wherein the emitted excitation pulse has a pulse width greater than 0.5 ns.

20. An apparatus as in any of the previous embodiments, wherein the emitted excitation pulse has a pulse width in the range of 1 ns to 20 ns.

21. An apparatus as in any of the previous embodiments, wherein the emitted excitation pulse has a pulse width of approximately 10 ns.

22. A system for performing time-resolved fluorescence imaging of a medium, the system comprising: (a) an illumination source, said illumination source comprising: (i) a light-emitting element configured to generate an excitation pulse into the medium; (ii) a pulse generator coupled to the light-emitting element via a transmission line; and (iii) a delay line coupled to the transmission line; (iv) wherein the delay line is configured to generate a reflected pulse into the transmission line to shape a decay profile of the excitation pulse; (b) a detector configured to receive one or more signals from the excited medium; (c) a processor coupled to the detector; and (d) programming executable on the processor and configured for analyzing the one or more signals from the excited medium.

23. A system as in any of the previous embodiments, wherein the delay line functions as a passive negative loop-back to deplete a trailing-edge charge within the light-emitting element.

24. A system as in any of the previous embodiments, wherein the delay line comprises a stub line.

25. A system as in any of the previous embodiments, wherein the reflected pulse from the delay line is configured to generate an excitation pulse with a controlled linear decay illumination profile.

26. A system as in any of the previous embodiments, wherein the shape and size of the stub line are configured to control the shape of the decay illumination profile.

27. A system as in any of the previous embodiments, wherein the light-emitting element comprises an LED.

28. A system as in any of the previous embodiments, wherein the emitted excitation pulse has a pulse width greater than 0.5 ns.

29. A system as in any of the previous embodiments, wherein the emitted excitation pulse has a pulse width in the range of 1 ns to 20 ns.

30. A system as in any of the previous embodiments, wherein the programming is further configured for: generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore; generating a second image of the medium at a specified time subsequent to said first image, said second image comprising data relating to at least the first fluorophore; and generating a third image as a function of the first image and the second image to identify a contrast between the first component and the second component within the medium.

31. A system as in any of the previous embodiments: wherein the second image is generated after decay of the second fluorophore such that data relating to the second fluorophore is absent from the second image; and wherein generating the third image comprises subtracting the first image from the second image such that data relating to the first fluorophore is absent from the second image.

32. A system as in any of the previous embodiments, wherein the second image is normalized to an intensity of the first image prior to subtracting the first image from the second image.

33. A system as recited in claim 30: wherein the second image is generated while the first and second fluorophores are still decaying; wherein the second image further comprises data relating to the second fluorophore; and wherein generating the third image comprises dividing the second image by the first image.

34. A system as in any of the previous embodiments, wherein the programming is further configured for: multiplying the third image by a constant.

35. A method for time-resolved fluorescence imaging of a sample medium, the method comprising: coupling a pulse generator to a light-emitting element via a transmission line; generating a pulse into the transmission line; combining a passive reflective pulse with the generated pulse; and emitting an excitation pulse from the light-emitting element; wherein the reflected pulse is configured to shape a decay profile of the excitation pulse.

36. A method as in any of the previous embodiments: wherein the reflective pulse is generated from a delay line coupled to the transmission line; and wherein the delay line functions as a passive negative loop-back to deplete a trailing-edge charge within the light-emitting element to shape the decay profile.

37. A method as in any of the previous embodiments, wherein the delay line comprises a stub line.

38. A method as in any of the previous embodiments, wherein the reflected pulse is configured to generate an excitation pulse with a controlled linear decay illumination profile.

39. A method as in any of the previous embodiments, wherein the shape and size of the stub line are configured to control the shape of the decay illumination profile.

40. A method as in any of the previous embodiments, wherein the light-emitting element comprises an LED.

41. A method as in any of the previous embodiments, wherein the medium comprises human tissue; and wherein the emitted excitation pulse has a pulse width greater than 0.5 ns.

42. A method as in any of the previous embodiments, wherein the emitted excitation pulse has a pulse width in the range of 1 ns to 20 ns.

43. A method as in any of the previous embodiments, further comprising: generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore; generating a second image of the medium at a specified time subsequent to said first image, said second image comprising data relating to at least the first fluorophore; and generating a third image as a function of the first image and the second image to identify a contrast between the first component and the second component within the medium.

44. A method as in any of the previous embodiments: wherein the second image is generated after decay of the second fluorophore such that data relating to the second fluorophore is absent from the second image; and wherein generating the third image comprises subtracting the first image from the second image such that data relating to the first fluorophore is absent from the second image.

45. A method as in any of the previous embodiments, wherein the second image is normalized to an intensity of the first image prior to subtracting the first image from the second image.

46. A method as in any of the previous embodiments: wherein the second image is generated while the first and second fluorophores are still decaying; wherein the second image further comprises data relating to the second fluorophore; and wherein generating the third image comprises dividing the second image by the first image.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for imaging a sample medium, the method comprising;
   exciting the sample medium with a square excitation light pulse;
   generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore;
   generating a second image of the medium at a specified time subsequent to said first image while the first fluorophore and second fluorophore still have decaying fluorescence values, said second image comprising data relating to the first fluorophore and the second fluorophore; and
   generating a third image as a function of first image and the second image to identify a lifetime-based contrast between the first component and the second component within the medium.

2. A method as recited in claim 1:
   wherein the second image is generated after decay of the second fluorophore such that data relating to the second fluorophore is absent from the second image; and
   wherein generating the third image comprises subtracting the first image from the second image such that data relating to the first fluorophore is absent from the second image.

3. A method as recited in claim 2, wherein the second image is normalized to the intensity of the first image prior to subtracting the first image from the second image.

4. A method as recited in claim 1:
   wherein generating the third image comprises dividing the second image by the first image.

5. A method as recited in claim 4, further comprising: multiplying the third image by a constant.

6. A method as recited in claim 1, wherein the sample medium comprises human tissue.

7. A system for imaging a sample medium, the system comprising:
   (a) a processor; and
   (b) programming executable on said processor and configured for:
      (i) exciting the sample medium with a square excitation light pulse;
      (ii) generating a first image of the medium, said first image comprising data relating to at least a first fluorophore corresponding to a first component of the medium and a second fluorophore corresponding to a second component of the medium, the first fluorophore having a longer fluorescence lifetime than the second fluorophore;
      (iii) generating a second image of the medium at a specified time subsequent to said first image while the first fluorophore and second fluorophore still have decaying fluorescence values, said second image comprising data relating to the first fluorophore and the second fluorophore; and
      (iv) generating a third image as a function of first image and the second image to identify a lifetime-based contrast between the first component and the second component within the medium.

8. A system as recited in claim 7:
   wherein the second image is generated after decay of the second fluorophore such that data relating to the second fluorophore is absent from the second image; and
   wherein generating the third image comprises subtracting the first image from the second image such that data relating to the first fluorophore is absent from the second image.

9. A system as recited in claim 8, wherein the second image is normalized to an intensity of the first image prior to subtracting the first image from the second image.

10. A system as recited in claim 7:
    wherein generating the third image comprises dividing the second image by the first image.

11. A system as recited in claim 10, wherein the programming is further configured for:
    multiplying the third image by a constant.

12. A system as recited in claim 7, wherein the sample medium comprises human tissue.

* * * * *